United States Patent
Han et al.

(10) Patent No.: US 10,928,301 B2
(45) Date of Patent: Feb. 23, 2021

(54) APPARATUS FOR MEASURING MOISTURE OF SOLID SAMPLE, METHOD FOR MEASURING MOISTURE CONTENT OF SOLID SAMPLE, AND METHOD FOR ANALYZING IMIDIZATION RATIO

(71) Applicant: LG Chem, Ltd., Seoul (KR)

(72) Inventors: Su Youn Han, Daejeon (KR); Byoung Hyoun Kim, Daejeon (KR); Dong Hyun Kim, Daejeon (KR); Hye Sung Cho, Daejeon (KR)

(73) Assignee: LG Chem, Ltd. (KR)

( * ) Notice: Subject to any disclaimer, the term of this patent is extended or adjusted under 35 U.S.C. 154(b) by 258 days.

(21) Appl. No.: 15/775,626

(22) PCT Filed: Apr. 27, 2017

(86) PCT No.: PCT/KR2017/004478
§ 371 (c)(1),
(2) Date: May 11, 2018

(87) PCT Pub. No.: WO2017/188746
PCT Pub. Date: Nov. 2, 2017

(65) Prior Publication Data
US 2018/0348115 A1 Dec. 6, 2018

(30) Foreign Application Priority Data
Apr. 27, 2016 (KR) .................. 10-2016-0051682

(51) Int. Cl.
*G01N 19/10* (2006.01)
*G01N 25/58* (2006.01)
(Continued)

(52) U.S. Cl.
CPC ............... *G01N 19/10* (2013.01); *G01N 1/20* (2013.01); *G01N 25/4826* (2013.01); *G01N 25/58* (2013.01); *G01N 33/442* (2013.01)

(58) Field of Classification Search
CPC ...... G01N 19/10; G01N 1/20; G01N 25/4826; G01N 25/58; G01N 33/442
(Continued)

(56) References Cited

U.S. PATENT DOCUMENTS 4,964,734 A * 10/1990 Yoshida ............... G01N 5/045
177/245
5,146,692 A * 9/1992 Ogiri .................... G01N 5/045
34/168
(Continued)

FOREIGN PATENT DOCUMENTS

JP      H07043267 A    2/1995
JP      H07043268 A    2/1995
(Continued)

OTHER PUBLICATIONS

Translation Description JP2005140591 (Year: 2005).*
(Continued)

*Primary Examiner* — Alexander A Mercado
*Assistant Examiner* — Monica S Young
(74) *Attorney, Agent, or Firm* — Lerner, David, Littenberg, Krumholz & Mentlik, LLP (57) ABSTRACT

The present invention relates to an apparatus for measuring moisture of a solid sample, a method for measuring a moisture content of the solid sample, and a method for analyzing an imidization rate, and more particularly, to an apparatus for measuring moisture of a solid sample, a method for measuring a moisture content of the solid sample, and a method for analyzing an imidization rate, which detect the moisture content of the solid sample at a
(Continued)

specific temperature by using a Karl-Fischer device capable of selectively detecting only the moisture content of the solid sample in the method for analyzing an imidization rate of the solid sample and calculate the imidization rate of the solid sample by using the detected moisture content.

14 Claims, 5 Drawing Sheets

(51) Int. Cl.
    *G01N 33/44*     (2006.01)
    *G01N 1/20*     (2006.01)
    *G01N 25/48*     (2006.01)

(58) Field of Classification Search
    USPC .............................................................. 73/73
    See application file for complete search history.

(56) References Cited

U.S. PATENT DOCUMENTS

| | | | | |
|---|---|---|---|---|
| 5,340,541 | A * | 8/1994 | Jackson | G01N 31/168 205/788 |
| 5,509,733 | A * | 4/1996 | Danley | G01N 25/4826 374/11 |
| 2001/0042439 | A1* | 11/2001 | Roberson, Jr. | H01L 21/67017 95/8 |
| 2015/0021158 | A1* | 1/2015 | Nakagawa | C10B 57/10 202/96 |
| 2016/0153713 | A1* | 6/2016 | Tsubata | F26B 5/06 34/298 |
| 2018/0136155 | A1* | 5/2018 | Balthes | G01N 33/15 |
| 2019/0131155 | A1* | 5/2019 | Bachlechner | H01L 21/67389 |

FOREIGN PATENT DOCUMENTS

| | | | |
|---|---|---|---|
| JP | H07043269 | A | 2/1995 |
| JP | H09316199 | A | 12/1997 |
| JP | 2000298126 | A | 10/2000 |
| JP | 2001188053 | A | 7/2001 |
| JP | 3314987 | B2 * | 8/2002 |
| JP | 2002286595 | A | 10/2002 |
| JP | 2005140591 | A * | 6/2005 |
| JP | 2005140591 | A | 6/2005 |
| JP | 2007043268 | A * | 2/2007 |
| KR | 20090091621 | A | 8/2009 |

OTHER PUBLICATIONS

Translation JP-2005140591 (Year: 2005).*
Translation JP 3314987 (Year: 2002).*
Translation JP2007043268 (Year: 2007).*
Search report from International Application No. PCT/KR2017/004478, dated Jul. 26, 2017.

* cited by examiner

APPARATUS FOR MEASURING MOISTURE OF SOLID SAMPLE, METHOD FOR MEASURING MOISTURE CONTENT OF SOLID SAMPLE, AND METHOD FOR ANALYZING IMIDIZATION RATIO

CROSS-REFERENCE TO RELATED APPLICATION(S)

The present application is a national phase entry under 35 U.S.C. § 371 of International Application No. PCT/KR2017/004478, filed on Apr. 27, 2017, which claims priority from Korean Patent Application No. 10-2016-0051682, filed on Apr. 27, 2016, the entire contents of which are incorporated herein by reference.

TECHNICAL FIELD

This application claims priority to and the benefit of Korean Patent Application No. 10-2016-0051682 filed in the Korean Intellectual Property Office on Apr. 27, 2016, the entire contents of which are incorporated herein by reference.

The present invention relates to an apparatus for measuring moisture of a solid sample, a method for measuring a moisture content of the solid sample, and a method for analyzing an imidization rate, and more particularly, to an apparatus for measuring moisture of a solid sample, a method for measuring a moisture content of the solid sample, and a method for analyzing an imidization rate, which detect the moisture content of the solid sample at a specific temperature by using a Karl-Fischer device capable of selectively detecting only the moisture content of the solid sample in the method for analyzing an imidization rate of the solid sample and calculate the imidization rate of the solid sample by using the detected moisture content.

Further, the present invention relates to an apparatus for measuring moisture of a solid sample, a method for measuring a moisture content of the solid sample, and a method for analyzing an imidization rate, which can measure an accurate moisture content included in the solid sample by increasing a temperature of a furnace unit to a high temperature and prevent an O-ring unit from being degenerated at the high temperature by separately forming a cooling unit that cools only the O-ring unit.

BACKGROUND ART

A polyimide film as a polymer synthesized from an aromatic diamine and aromatic dianhydride is an amorphous polymer having excellent insulation property, heat resistance and weatherability. Therefore, the polyimide film is used in a wide range of industrial fields such as aerospace, automobile, adhesive and coating, and electronic materials because the polyimide film is much lighter and has stronger mechanical properties and lower thermal expansion than metal.

The polyimide film is prepared by imidization through heat treatment in a polyamic acid state which is a precursor, and it is difficult to control the imidization degree in an actual process, and the polyamic acid as the precursor remains in an imide film.

Therefore, studies on the imidization with temperature and time have been carried out in order to clarify an imidization rate of the polyamic acid, and studies on a residual solvent have also been carried out in an imidization process.

A method for clarifying the imidization rate includes an FT-IR method and an EGA-MS method and the FR-IR method is a method that determines the imidization degree by removing water and DAMc evaporated when an imidization reaction occurs at each temperature to evaporate a polyamide film and verifying a characterization peak of the polyamide film.

Further, the EGA-MS method is a method that calculates the imidization rate by measuring the content of moisture evaporated as a by-product when the polyamic acid is cured to the polyimide.

However, the FT-IR method as a method for calculating a relative imidization rate has a problem that a result value of the imidization degree is not accurate when a curing degree of the polyamic acid is not 100% and the EAG-MS method has a problem that it is difficult to treat the solid sample because the amount of the solid sample which may be measured is in the range of approximately 10 to 30 mg.

Further, both methods have a problem that when the solid sample is heated up to the high temperature, a shape of a sealant sealed to an inlet of a fixing unit fixing the solid sample is deformed, and as a result, a temperature of a furnace heating the solid sample may not be maintained.

Moreover, an EGC-MS analysis method has a problem that a program and an apparatus which may measure the moisture content and the imidization rate of the solid sample by performing purging in a predetermined temperature section and thereafter, collecting the moisture evaporated in a next temperature section are not included. Therefore, a problem that a moisture value evaporated in a low-temperature section needs to be subtracted at the time of calculating the imidization rate may occur.

Accordingly, the present inventors have contrived the apparatus for measuring the moisture of the solid sample, which may heat the solid sample up to the high temperature by improving the existing method for measuring the imidization rate of the solid sample.

DETAILED DESCRIPTION OF THE INVENTION

Technical Problem

The present invention is contrived to solve the problem and the present invention has been made in an effort to provide an apparatus for measuring moisture of a solid sample, combine a solid sample curing unit heating and cooling the solid sample and Carl-Fischer equipment measuring a moisture content evaporated when the solid sample is heated to measure moisture which may be included on the surface of the solid sample and automatically exclude the corresponding moisture at the time of measuring the imidization rate without a limit in amount of the solid sample which is measurable.

Further, the present invention has been made in an effort to provide a method for measuring a moisture content of a solid sample and a method for analyzing an imidization rate, which can analyze the imidization rate by using the moisture generated when the solid sample is cured to calculate an absolute imidization rate and analyze an accurate imidization rate value even when a curing degree is not 100%.

Moreover, the present invention has been made in an effort to provide an apparatus for measuring moisture of a solid sample, a method for measuring a moisture content of a solid sample, and a method for analyzing an imidization rate, which position an O-ring cooling unit on the periphery of an O-ring unit sealed in order to maintain an internal temperature of a furnace unit capable of heating or cooling the solid sample to prevent a shape or a property of the O-ring unit from being deformed at a high temperature and increase the solid sample up to the high temperature at the time of heating the solid sample.

Technical Solution

In order to solve the problem, an apparatus for measuring moisture of a solid sample according to the present invention, includes: an introduction unit into which the solid sample is introduced; a furnace unit to which the solid sample is fixed and which heats and cools the solid sample; an O-ring unit sealed between the introduction unit and the furnace unit; a three-way valve connected with a moisture transport pipe formed in the furnace unit and receiving and controlling moisture evaporated from the solid sample; and a Karl-Fischer unit measuring a detected moisture content of the solid sample by using the moisture transported through a metering transport pipe formed in the three-way valve and the O-ring unit includes an O-ring cooling unit positioned outside the O-ring unit and cooling the O-ring unit.

Preferably, the furnace unit includes a body fixing the solid sample, a heating unit positioned outside the body and heating the body, and a cooling unit positioned outside the body and cooling the body.

Preferably, the furnace unit includes a moisture transport gas pipe in which moisture transport gas is supplied and the moisture transport gas transports the moisture evaporated from the solid sample to the three-way valve.

Preferably, a moisture trap unit is included in the moisture transport gas pipe to remove the moisture included in the moisture transport gas.

Preferably, the cooling unit and the O-ring cooling unit cool the body and the O-ring unit by using at least one of a water cooling type and an air cooling type.

Preferably, the three-way valve includes a moisture transport valve in which the moisture evaporated from the solid sample fixed to the furnace unit is transported, a purge valve in which the moisture supplied from the furnace unit is transported to the outside, and a metering valve in which the moisture supplied from the furnace unit is transported to the Karl-Fischer unit.

Preferably, the apparatus for measuring moisture of a solid sample further includes a control unit controlling a threshold temperature of the furnace unit by controlling the heating unit and the cooling unit and controlling the three-way valve.

Preferably, the control unit heats the furnace unit by setting a temperature of the heating unit to at least one temperature of a first threshold temperature, a second threshold temperature, and a third threshold temperature, and cools the furnace unit by setting the temperature of the cooling unit to at least one temperature of a reference temperature and the first threshold temperature.

Preferably, the control unit controls the purge valve to be on and the metering valve to be off when the furnace unit is heated up to the first threshold temperature or heated up to the third threshold temperature or higher, and controls the purge valve to be off and the metering valve to be on when the furnace unit is heated up to the second threshold temperature and the third threshold temperature.

A method for measuring a moisture content of a solid sample according to the present invention includes: preparing the solid sample; fixing the solid sample to a body of a furnace unit and heating the body; transporting moisture evaporated from the solid sample to a three-way valve and transporting the evaporated moisture to the outside or a Karl-Fischer unit; cooling the body; and measuring a detected moisture content of the solid sample through the moisture transported to the Karl-Fischer unit and in the cooling of the body, an O-ring unit positioned between an introduction unit and the body is cooled.

Preferably, the heating of the body includes heating the body from a reference temperature up to a first threshold temperature, heating the body from the first threshold temperature up to a second threshold temperature, and heating the body from the second threshold temperature up to a third threshold temperature.

Preferably, the transporting of the evaporated moisture to the outside or the Karl-Fischer unit includes transporting the evaporated moisture to the outside by controlling, by a control unit, a purge valve to be on and a metering valve to be off in the three-way valve when the body is at the first threshold temperature, transporting the evaporated moisture to the Karl-Fischer unit by controlling, by the control unit, the purge valve to be off and the metering valve to be on when the body is at the second threshold temperature, transporting the evaporated moisture to the Karl-Fischer unit by controlling, by the control unit, the purge valve to be off and the metering valve to be on when the body is at the third threshold temperature, and transporting the evaporated moisture to the outside by controlling, by the control unit, the purge valve to be on and the metering valve to be off when the body is at the third threshold temperature or higher.

Preferably, the cooling of the body includes cooling the body at at least one temperature of the reference temperature and the first threshold temperature by introducing at least one of gas and liquid into a cooling unit positioned outside the body.

A method for analyzing an imidization rate of a solid sample according to the present invention may further include analyzing the imidization rate of the solid sample by using the detected moisture.

Preferably, in the analyzing of the imidization rate, the imidization rate is analyzed by using a detected moisture content evaporated when the body is at at least one of a second threshold temperature and a third threshold temperature.

Preferably, in the analyzing of the imidization rate, the imidization rate is calculated to correspond to a variable determined based on an equation given below.

$$DI\ (\%) = \frac{W_{PI}/MW_{PI}}{W_{H2O}(M_{H2O} \times 18) + W_{PI}/MW_{PI}} \quad \text{[Equation 1]}$$

Herein, DI represents the imidization rate, $W_{H2O}$ represents the detected moisture content (g), $M_{H2O}$ represents mol of $H_2O$ evaporated per unit, $W_{PI}$ represents polyimide mass (g) in the solid sample, $MW_{PI}$ represents a molecular weight of the polyimide unit, and $W_{sample}$ represents measured solid sample mass (g).

Advantageous Effects

An apparatus for measuring moisture of a solid sample, a method for measuring a moisture content of the solid sample, and a method for analyzing an imidization rate according to the present invention combine a solid sample curing unit heating and cooling the solid sample and Carl-Fischer equipment measuring a moisture content generated when the solid sample is heated to purge moisture included on the surface of the solid sample to the outside and automatically exclude the corresponding moisture at the time of measuring the imidization rate without a limit in amount of the solid sample which is measurable.

Further, the imidization rate is analyzed by using the moisture generated when the solid sample is cured to calculate an absolute imidization rate and even when a curing degree is not 100%, an accurate imidization rate value can be analyzed.

Moreover, an O-ring cooling unit is positioned on the periphery of an O-ring unit sealed in order to maintain an internal temperature of a furnace unit capable of heating or cooling the solid sample to prevent a shape or a property of the O-ring unit from being deformed at a high temperature and increase the temperature of the solid sample up to the high temperature at the time of heating the solid sample.

BRIEF DESCRIPTION OF DRAWINGS

FIG. 5(a) illustrates the experimental result of PI film 1, FIG. 5(b) illustrates a result of PI film 2, and FIG. 5(c) illustrates the result of PI film 3. FIG. 5(d) is a graph of comparing imidization rate graphs for each of temperatures of PI films 1 to 3.

BEST MODE

Hereinafter, preferred embodiments of an apparatus for measuring moisture of a solid sample, a method for measuring a moisture content of the solid sample, and a method for analyzing an imidization rate of the solid sample according to embodiments of the present invention will be described with reference to the accompanying drawings. In this process, thicknesses of lines and sizes of constituent elements illustrated in the drawings, and the like may be exaggerated for clarity and ease of description. Further, terms to be described below, as terms which are defined in consideration of functions in the present invention may vary depending on the intention or custom of a user or an operator. Accordingly, definitions of the terms need to be described based on contents throughout this specification.

Figure 1:
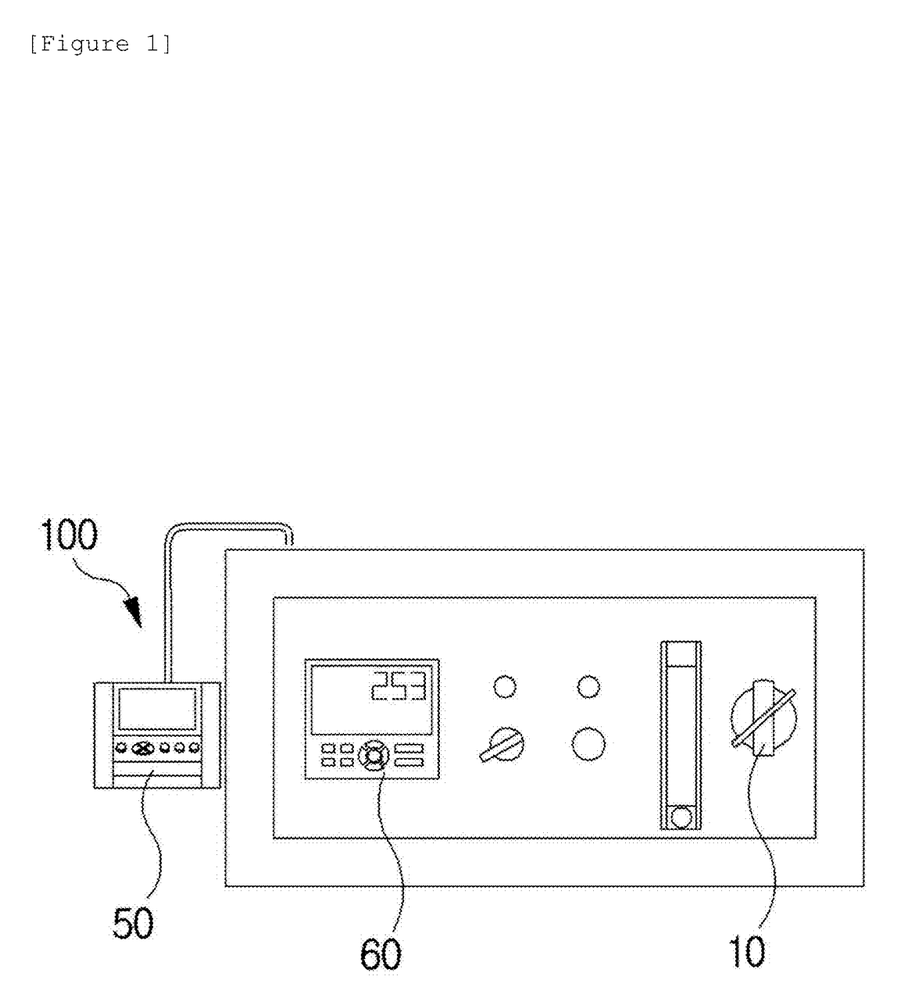
FIG. 1 is a front view illustrating a structure of an apparatus for measuring moisture of a solid sample.
Figure 2:
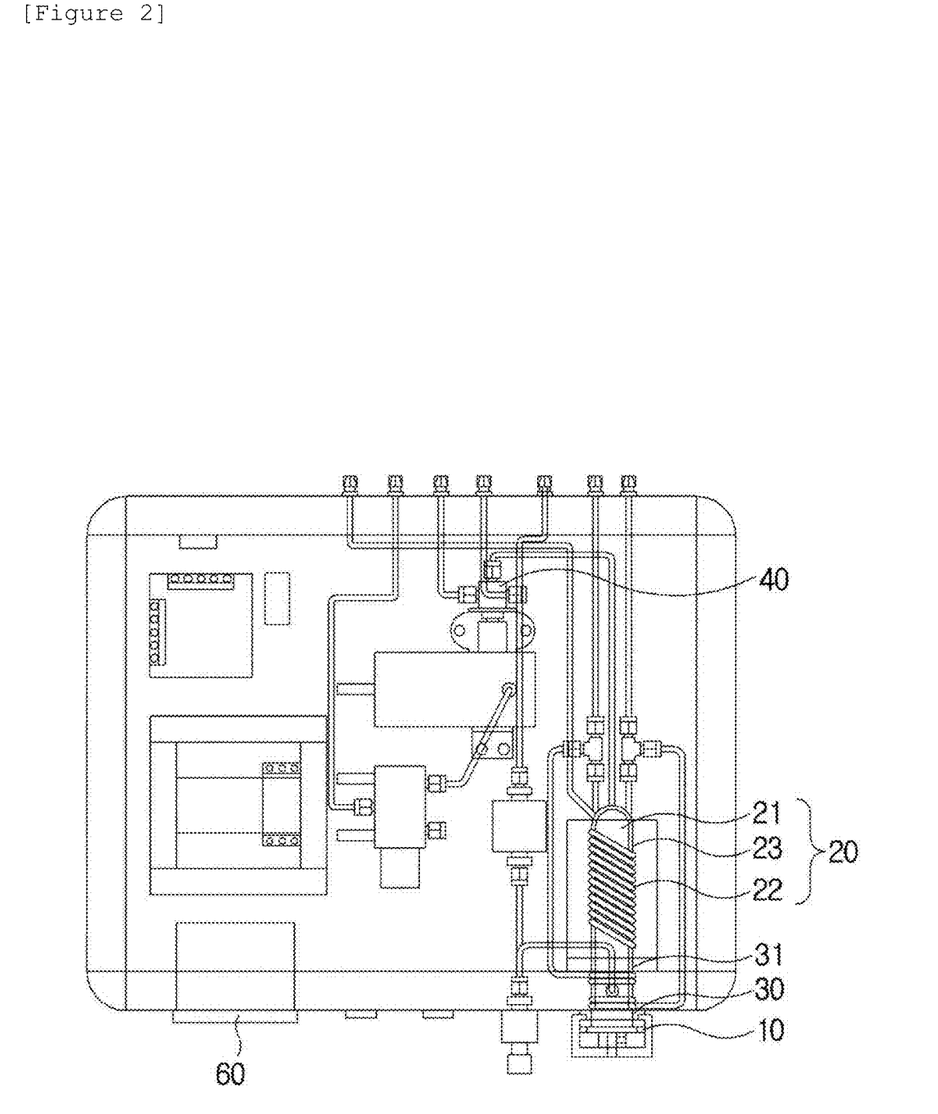
FIG. 2 is a plan view illustrating the structure of a solid sample heating unit.
Figure 3:
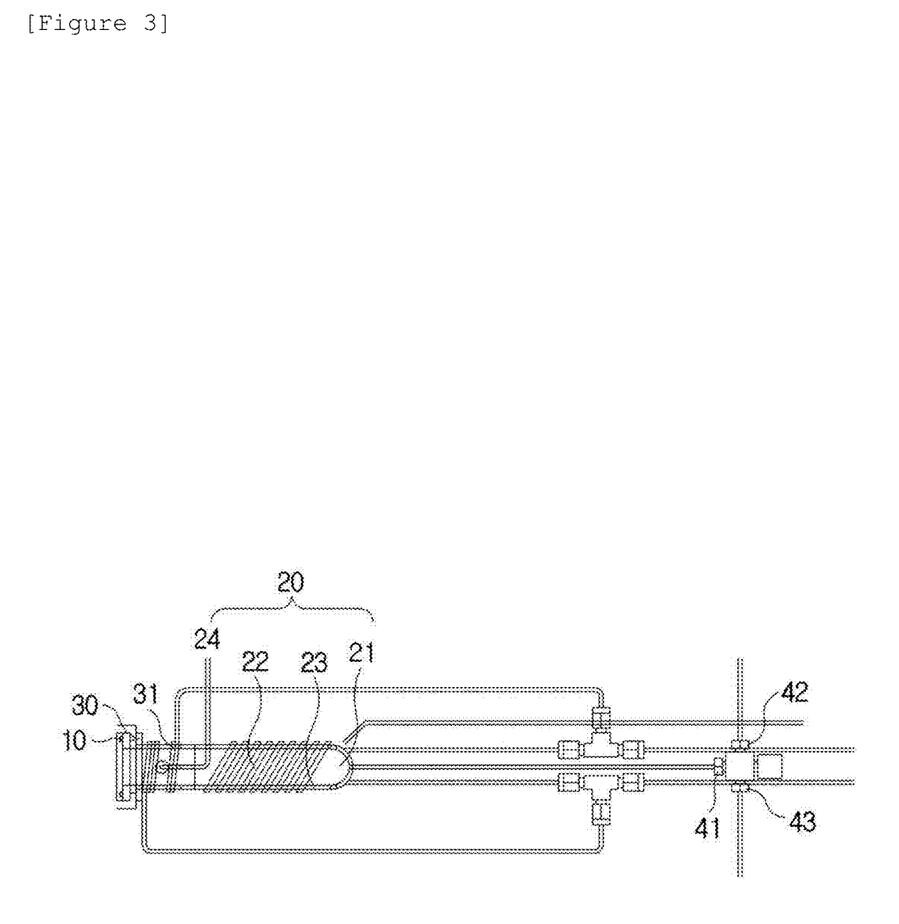
FIG. 3 is a structural diagram illustrating a connection relationship of an introduction unit, a furnace unit, an O-ring unit, and a 3-way valve.

FIG. 1 is a front view illustrating a structure of an apparatus 100 for measuring moisture of a solid sample, FIG. 2 is a plan view illustrating the structure of a solid sample curing unit (not illustrated), and FIG. 3 is a structural diagram illustrating a connection relationship of an introduction unit 10, a furnace unit 20, an O-ring unit 30, and a 3-way valve 40.

The apparatus 100 for measuring moisture of a solid sample, which is illustrated in FIG. 1 is an apparatus as a structure generally including a solid sample curing unit and a Carl-Fischer unit 50, which measures a detected moisture content of the solid sample by evaporating the moisture generated when the solid sample is cured by the solid sample curing unit and moving the evaporated moisture to the Carl-Fischer unit 50 through a movement pipe.

Referring to FIG. 2, the solid sample curing unit may include the introduction unit 10 in which the solid sample is introduced, the furnace unit 20 to which the solid sample is fixed and which heats and cools the solid sample, the O-ring 30 sealed between the introduction unit 10 and the furnace unit 20, the 3-way valve 40 connected with a moisture transport pipe formed in the furnace unit 20 and receiving and controlling the moisture evaporated from the solid sample, a control unit 60 controlling a threshold temperature of the furnace unit 20 by controlling a heating unit 22 and a cooling unit 23 and controlling the three-way valve 40, a terminal block (not illustrated) including one or more electric connectors, and a power controller (not illustrated). Furthermore, the O-ring unit 30 may include an O-ring cooling unit 31 positioned outside the O-ring unit 30 and cooling the O-ring unit 30.

Referring to FIG. 3, the introduction unit 10 serves as an inlet of the furnace unit 20 and an opening/closing device may be formed in the introduction unit 10. Moreover, since the introduction unit 10 uses the existing known technology, a detailed description thereof will be omitted.

In addition, the furnace unit 20 may include a body 21 fixing the solid sample, the heating unit 22 positioned outside the body 21 and heating the body 21, and the cooling unit 23 positioned outside the body 21 and cooling the body 21. It should be noted that the body 21 is formed in a size of a degree to accommodate a tray to which the solid sample may be fixed. Therefore, the moisture of the solid sample may be measured without a limit in amount of the solid sample which is measurable.

Furthermore, the heating unit 22 may be heated by a heating body heated by receiving electricity or heat from the outside or a heating pipe heating the body 21 through introduction of heated gas/liquid through a pipe, but may be substituted with another heating method that may heat the furnace unit 20 and is not limited thereto.

Moreover, the cooling unit 23 may cool the body 21 by using at least one of a water-cooling type and an air-cooling type. That is, the furnace unit 20 may include a cooling liquid introduction pipe, a cooling gas introduction pipe, and a waster refrigerant discharge pipe and the furnace unit 20 may be cooled by the water cooling type when a cooling liquid is introduced through the cooling liquid introduction pipe, the air cooling type when cooling gas is introduced through the cooling gas introduction pipe, and a mixing type in which the water cooling type and the air cooling type are merged when the cooling liquid and the cooling gas are introduced through the cooling liquid introduction pipe and the cooling gas introduction pipe. In this case, waste cooling liquid and water cooling gas may be discharged to the outside through the waster refrigerant discharge pipe.

Herein, it is preferable that the cooling liquid is composed of distilled water and the cooling gas is composed of nitrogen, but the cooling liquid and the cooling gas may be substituted with other liquid and gas capable of cooling the furnace unit 20 and are not limited thereto.

Further, when the furnace unit 20 is cooled by the mixing type in which the air cooling type and the water cooling type are merged, the temperature of the furnace unit 20 may be decreased up to a target temperature within a shorter time than natural cooling, the water cooling type, or the air cooling type.

For example, when a cooling time of the natural cooling, the air cooling type, the water cooling type, and the method in which the air cooling type and the water cooling type are merged is measured, the furnace unit is cooled from 450° C. up to 50° C. and the cooling time is measured as 80 to 100 minutes in the case of the natural cooling, as 50 to 70 minutes in the case of the air cooling type, as 20 to 40 minutes in the case of the water cooling type, and as 3 to 6 minutes in the case of the method in which the air cooling type and the water cooling type are merged. It may be verified that the cooling time in the merge method is approximately 15 times or even shorter than that in the natural cooling and approximately 5 times or even shorter than the water cooling type.

Further, the furnace unit 20 may include a moisture transport gas pipe 24 through which moisture transport gas is supplied and the moisture transport gas may transport the moisture evaporated in the solid sample to the three-way valve 40. Furthermore, the moisture transport gas needs to satisfy an anhydrous condition in order to transport only the moisture evaporated in the solid sample, and as a result, it should be noted that the moisture transport gas pipe 24 may include a moisture trap unit (not illustrated). The moisture trap unit serves to remove the moisture included in the moisture transport gas.

Next, the O-ring unit 30 as a component that increases watertightness and airtightness by filling or inserting gaps of the introduction unit 10 and the furnace unit 20 may be composed of at least one composition of a synthetic resin, an oil-based caulking, a silicon, and rubber, but may be substituted with another composition which perform a similar function and is not limited thereto.

Moreover, the O-ring unit 30 includes an O-ring cooling unit 31 and the O-ring cooling unit 31 is positioned in a space formed on the periphery of the O-ring unit 30 to cool the O-ring unit 30 by using at least one of the water cooling type and the air cooling type by using the cooling liquid and the cooling gas introduced into the cooling liquid introduction pipe and the cooling gas introduction pipe. Further, the cooling liquid and the cooling gas that cools the O-ring unit 30 may be discharged to the outside through the water refrigerant discharge pipe. Since the cooling liquid introduction pipe, the cooling gas introduction pipe, and the water refrigerant discharge pipe include separation valves, it should be noted that the introduced cooling liquid and gas may be separately introduced into the cooling unit 23 and the O-ring cooling unit 31.

Furthermore, a space is formed outside the O-ring unit 30 to constitute the O-ring cooling unit 31, and as a result, when the furnace unit 20 is heated in order to cure the solid sample, the O-ring unit 30 may be prevented from being deformed at the high temperature of 200 to 500° C. and the solid sample may be cured at the high temperature of 200° C. or higher. Therefore, the moisture generated when the solid sample is cured may be maximally detected.

Next, in the three-way valve 40, an air storage unit (not illustrated) and an air supply unit (not illustrated) are positioned outside the three-way valve 40 to store air introduced from the outside in the air storage unit and thereafter, in order transport the moisture transported to the three-way valve 40 to the outside or the Carl-Fischer unit 50, the air supply unit supplies air to the three-way valve 40 to provide power for transporting the moisture.

Moreover, since the moisture transport air needs to satisfy the anhydrous condition, the trap unit removing the moisture may be included in at least one of the air storage unit and the air supply unit.

Furthermore, the three-way valve 40 may include a moisture transport valve 41 in which the moisture generated from the solid sample fixed to the furnace unit 20 is transported, a purge valve 42 in which the moisture supplied in the furnace unit 20 is transported to the outside, and a metering valve 43 in which the moisture supplied in the furnace unit 20 is transported to the Karl-Fischer unit 50.

The Karl-Fischer unit 50 positioned outside the solid sample curing unit may measure the detected moisture content of the solid sample by using the moisture transported through a metering transport pipe formed in the three-way valve 40. Further, since the existing known technology is used as a technology that measures the detected moisture content of the solid sample by using the Karl-Fischer unit 50, a detailed description thereof will be omitted.

The control unit 60 sets the temperature of the heating unit 22 to at least one temperature of a first threshold temperature, a second threshold temperature, and a third threshold temperature to heat the furnace unit 20 and sets the temperature of the cooling unit 23 to at least one temperature of a reference temperature and the first threshold temperature to cool the furnace unit 20. Further, the control unit 60 may control the three-way valve 40 to be on/off at at least any one temperature of the first threshold temperature, the second threshold temperature, and the third threshold temperature.

In more detail, when the furnace unit 20 is heated up to the first threshold temperature or heated at the third threshold temperature or higher, the control unit 60 may control the purge valve 42 to be on and control the metering valve 43 to be off and when the furnace unit 20 is heated up to the second threshold temperature and the third threshold temperature, the control unit 60 may control the purge valve 42 to be off and control the metering valve 43 to be on.

In this case, when the moisture generated in a first threshold temperature section is evaporated to the outside at a room temperature which is a low-temperature unit, and as a result, the moisture content of the solid sample is measured in the Karl-Fischer unit 50, the moisture content which may be included in the surface of the solid sample may be excluded.

Moreover, a temperature measuring device formed in the furnace unit 20 may transmit data regarding the temperature of the furnace unit 20 to the control unit 60 and the control unit 60 may control the temperature of the furnace unit 20 and the three-way valve 40 through the received data.

Furthermore the temperature measuring device may further include a display unit in order to control the heating unit 22, the cooling unit 23, and the three-way valve 40 and the temperature of the furnace unit 20 and an on/off temperature of the three-way valve 40 may be set through the display unit.

Herein, it should be noted that a threshold temperature is not limited to the first to third threshold temperatures, but may be set to fourth, and fifth to N-th (N is a natural number) threshold temperatures.

Since the terminal block and the power controller use the existing known technology, the detailed description thereof will be omitted.

The present invention may further include a calculation unit (not illustrated) and may be applied to the apparatus for measuring an imidization rate of the solid sample, which may automatically measure the imidization rate of the solid sample. In more detail, the data regarding the detected moisture content of the solid sample, which is detected by the apparatus 100 for measuring the moisture of the solid sample may be transmitted to the calculation unit and the calculation unit that receives the data may calculate the imidization rate of the solid sample.

When the moisture of the solid sample is measured, the moisture evaporated at the time of heating the furnace unit 20 up to the first threshold temperature is purged to the outside, and as a result, error values may be reduced at the time of measuring the moisture of the solid sample and measuring the imidization rate by evaporating the moisture included in the surface of the solid sample to the outside. Further, at the time of calculating the imidization rate, a labor that the moisture content of the solid sample evaporated in the section in which the room temperature is heated up to the first threshold temperature needs to be excluded through the calculation unit at the time of calculating the imidization rate may be reduced.

A method for measuring a moisture content of the solid sample according to the present invention may include a step (S101) of preparing the solid sample, a step (S201) of fixing the solid sample to the body 21 of the furnace unit and heating the body 21, a step (S301) of transporting the moisture evaporated in the solid sample to the three-way valve 40 and transporting the evaporated moisture to the outside or to the Karl-Fischer unit 50, a step (S401) of cooling the body 21, and a step (S501) of measuring the detected moisture content of the solid sample through the moisture transported to the Karl-Fischer unit 50 and it should be noted that in the step (S401) of cooling the body 21, the O-ring unit 30 positioned between the introduction unit 10 and the body 21 may be cooled.

The step (S101) of preparing the solid sample is a step of preparing the solid sample which includes the moisture, in which the moisture may be evaporated by heating or which may be imidized by the heating. Herein, if the solid sample includes the solid sample used in the art, the solid sample is not limited.

The step (S201) of heating the body 21 may further include a step (S211) of heating the body 21 from the reference temperature up to the first threshold temperature, a step (S221) of heating the body 21 from the first threshold temperature up to the second threshold temperature, and a step (S231) of heating the body 21 from the second threshold temperature up to the third threshold temperature.

In this case, the first threshold temperature is preferably 30 to 60° C., the second threshold temperature is preferably 130 to 200° C., and the threshold temperature is preferably 400 to 500° C.

Further, it should be noted that the reference temperature may be increased up to the first threshold temperature for 3 to 8 minutes, the first threshold temperature may be increased up to the second threshold temperature for 10 to 20 minutes, and the second threshold temperature may be increased up to the third threshold temperature for 30 to 40 minutes.

The step (S301) of transporting the evaporated moisture to the outside or the Karl-Fischer unit 50 may further include a step (S311) of transporting the evaporated moisture to the outside by controlling, by the control unit 60, the purge valve 42 in the three-way valve 40 to be on and the metering valve 43 to be off when the body 21 is at the first threshold temperature, a step (S321) of transporting the evaporated moisture to the Karl-Fischer unit 50 by controlling, by the control unit 60, the purge valve 42 to be off and the metering valve 43 to be on when the body 21 is at the second threshold temperature, a step (S331) of transporting the evaporated moisture to the Karl-Fischer unit 50 by controlling, by the control unit 60, the purge valve 42 to be off and the metering valve 43 to be on when the body 21 is at the third threshold temperature, and a step (S341) of transporting the evaporated moisture to the outside by controlling, by the control unit 60, the purge valve 42 to be on and the metering valve 43 to be off when the body 21 is at the third threshold temperature or higher.

In this case, when the body 21 is at the first threshold temperature, the control unit 60 controls the purge valve 42 in the three-way valve 40 to be on and the metering valve 43 to be off, and as a result, the error values at the time of measuring the moisture of the solid sample and measuring the imidization rate may be reduced by evaporating the moisture included in the surface of the solid sample to the outside by the step (S311) of transporting the evaporated moisture to the outside.

Furthermore, it should be noted that a flow rate of the moisture transport gas supplied through the moisture transport gas pipe 24 may be set to 10 mL/min to 300 mL/min.

In a step (S401) of cooling the body 21, at least one of the gas and the liquid is introduced into the cooling unit 23 positioned outside the body 21 to cool the body 21 to at least one temperature of the reference temperature and the first threshold temperature.

A method for analyzing an imidization rate of the solid sample according to the present invention may include a step (S501) of analyzing the imidization rate of the solid sample by using the detected moisture content measured by the method for measuring the moisture content of the solid sample.

In the step (S501) of analyzing the imidization rate of the solid sample, the imidization rate may be analyzed by using the detected moisture content evaporated when the body 21 is at at least one of the second threshold temperature and the third threshold temperature and the imidization rate may be calculated to correspond to a variable determined based on an equation given below.

$$DI\ (\%) = \frac{W_{PI}/MW_{PI}}{W_{H2O}(M_{H2O} \times 18) + W_{PI}/MW_{PI}} \quad [\text{Equation 1}]$$

Herein, DI represents the imidization rate, $W_{H2O}$ represents the detected moisture content (g), $M_{H2O}$ represents mol of $H_2O$ evaporated per unit, $W_{PI}$ represents polyimide mass (g) in the solid sample, $MW_{PI}$ represents a molecular weight of the polyimide unit, and $W_{sample}$ represents measured solid sample mass (g).

Experimental Example 1: Analysis of Bubble Generation Cause of Solid Sample

A bubble generation cause of an LC film for a sun roof was analyzed. A bubble generation cause analysis experiment was performed by a method that classifies the LC film for each material and thereafter, measures a moisture amount generated when respective materials are heated at the high temperature.

In this case, as an apparatus for measuring the moisture amounts of the respective materials, the apparatus for measuring the moisture of the solid sample was used.

In more detail, the respective materials were fixed to the body 21 of the furnace unit and thereafter, the temperature of the body 21 was increased up to 50° C. In this case, the moisture evaporated from the material was purged to the outside.

Next, the body was heated from 50° C. up to 120° C. and thereafter, the temperature of 120° C. was maintained for 1 hour. The moisture generated in this case was transported to the Karl-Fischer unit 50 to measure the detected moisture content of the material.

A result of measuring the detected moisture contents detected in the respective materials is shown in a table given below.

TABLE 1

| | Samples | Sample content (mg) | Moisture content (µg) | Moisture content (%) |
|---|---|---|---|---|
| 1 | Polarizing plate material 1 | 213.8 | 3618.3 | 1.7 |
| 2 | Polarizing plate material 2 | 169.1 | 3528.5 | 2.1 |
| 3 | TAC 1 | 175.5 | 995.2 | 0.6 |
| 4 | TAC 2 | 254.7 | 606.0 | 0.2 |
| 5 | Material for LC cell: PET 1 | 225.4 | 413.7 | 0.2 |
| 6 | Material for LC cell: COP 1 | 218.2 | 41.9 | <0.05 |
| 7 | Material for LC cell: PC 1 | 213.4 | 250.0 | 0.1 |
| 8 | Material for LC cell: COP 2 | 23.4 | 30.9 | <0.05 |
| 9 | Material for LC cell: PET 1 | 231.2 | 397.9 | 0.2 |
| 10 | Material for LC cell: PET 2 | 219.5 | 452.5 | 0.2 |
| 11 | Liquid crystal film 1 | 230.4 | 650.4 | 0.3 |
| 12 | Material for LC cell: COP 2 | 216.6 | 27.8 | <0.05 |
| 13 | Adhesive 1 | 270.7 | 482.2 | 0.2 |
| 14 | Adhesive 2 | 100.0 | 80.3 | 0.08 |
| 15 | Adhesive 3 | 67.6 | 46.5 | 0.07 |

The most moisture contents were measured in 'polarizing plates 1 and 2' among the LC film materials, and as a result, the most moisture contents may cause the bubbles to be generated in the LC film.

As the moisture content of 'the material for the LC cell: COP 1 and COP 2 films' among the LC film materials, a smallest value of 0.05% or less was detected.

Experimental Example 2: Measurement of Moisture Detection Content Depending on Solid Sample Quantity The furnace unit 20 used 1% K/F oven standard (Na2WO4 2H2O) and the flow rate of the moisture transport gas (He) was set to 100 mL/min.

In the experimental method, the temperature was increased from 25° C. up to 50° C. at a velocity of 10° C./min and thereafter, the moisture evaporated in this case was purged to the outside.

The temperature was increased from 50° C. up to 450° C. at the velocity of 10° C./min and the moisture evaporated in this case was transported to the Karl-Fischer unit 50 to measure the solid sample moisture detection amount. It is noted that the moisture generated at 450° C. or higher is purged to the outside.

The weight of the solid sample was set to 11.8, 20.5, 31, 58, 102, 401 and 704 mg and the experiment was performed according to each solid sample quantity.

The experimental result of measuring the moisture detection amount depending on the sample quantity is shown in a table given below.

TABLE 2

| Standard item amount (mg) | K/F moisture detection amount (µg) |
|---|---|
| 11.8 | 180 |
| 20.5 | 227 |
| 31 | 350 |
| 58 | 628 |
| 102 | 1087 |
| 401 | 4033 |
| 704 | 7053 |

Figure 4:
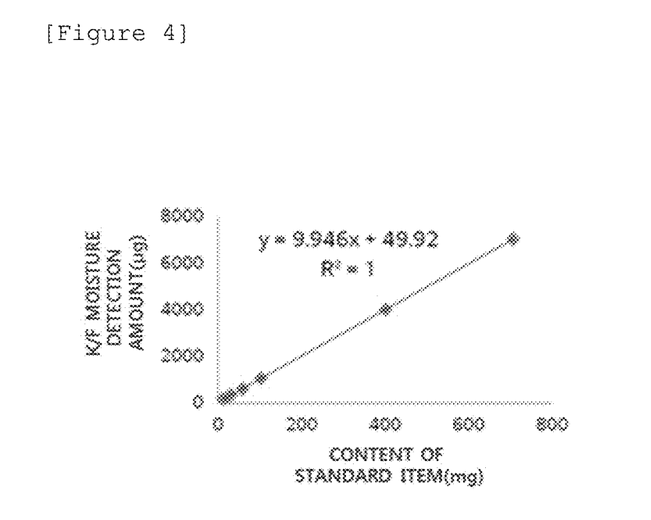
FIG. 4 is a calibration curve graph illustrating a result of measuring a moisture detection content of the solid sample depending on the amount of the solid sample.

Referring to FIG. 4, as described in Experimental Example 1, a standard item is cured by using a K/F oven standard, and as a result, it may be verified that the moisture detection amount increases in proportion to the amount of the standard item. This may mean that when the K/F oven standard is used, the amount of the moisture generated at the time of curing the solid sample may be maximally detected, and as a result, an error range of the imidization rate analyzed by Equation 1 may be minimum.

Example 1

The polyimide film was generated by heating polyacrylamide and an experiment of measuring the moisture detection content and the imidization rate for each threshold temperature was performed in order to detect the moisture generated at the time of curing the polyimide film.

The experiment was performed according to the method for analyzing the imidization rate of the solid sample, the furnace unit 20 used HYDRANAL-Coulomat AG-Oven (Sigma-Aldrich, CN:34739-500ML-R), an extraction time was set to 300 s, a Start drift value was set to a value less than 20 µg/min, and a stop time was set to OFF. In this case, it is noted that the Start drift value may be preferably maintained at 10 µg/min.

The control unit 60 set the threshold temperature to 50° C., 200° C., 250° C., 300° C., 350° C., and 450° C. It is noted that the moisture generated during a process in which the temperature is increased from the room temperature up to 50° C. is purged to the outside in order to evaporate the moisture included in the surface of the polyacrylamide and the furnace unit 20.

By performing the measurement of the moisture content and the imidization rate for each temperature each twice, an average of the imidization rate was measured.

A solid sample polymerization structure of BPDA-PDA PI film 1 of Example 1 and the moisture content and the imidization rate generated for each temperature when BPDA-PDA PI film 1 is polymerized are described below. It is noted that MWpaa of PI film 1 is 402.36 and MWPI of PI film 1 is 366.34.

TABLE 3

| Curing temperature (° C.) | Sample amount (mg) | Moisture content (µg) | DI (%) | DI (%) average value |
|---|---|---|---|---|
| 200 | 256.5 | 6635.7 | 73.0 | 73.0 |
|  | 259.4 | 6684.2 | 73.1 |  |
| 250 | 234.9 | 2576.3 | 88.7 | 88.6 |
|  | 232.2 | 2609.6 | 88.4 |  |
| 300 | 235.3 | 2236.4 | 90.2 | 89.7 |
|  | 230.2 | 2437.7 | 89.1 |  |
| 350 | 234.5 | 2102.0 | 90.8 | 90.8 |
|  | 208.8 | 1867.0 | 90.8 |  |

TABLE 3-continued

| Curing temperature (° C.) | Sample amount (mg) | Moisture content (µg) | DI (%) | DI (%) average value |
|---|---|---|---|---|
| 450 | 249.2 | 510.3 | 97.9 | 98.0 |
|  | 248.4 | 456.7 | 98.1 |  |

Example 2

The experiment was performed under the same condition as Example 1 and the solid sample polymerization structure of BPDA/ODPA-PDA/ODA PI film 2 of Example 2 and the moisture content and the imidization rate generated for each temperature when BPDA/ODPA-PDA/ODA PI film 2 are polymerized are described below. It is noted that MWpaa of PI film 2 is 912.82 and MWPI of PI film 2 is 840.76.

Molecular Weight 912.82

TABLE 4

| Curing temperature (° C.) | Sample amount (mg) | Moisture content (µg) | DI (%) | DI (%) average value |
|---|---|---|---|---|
| 200 | 267.8 | 3087.4 | 86.4 | 86.5 |
|  | 257.4 | 2926.4 | 86.6 |  |
| 250 | 257.8 | 1962.1 | 91.0 | 91.6 |
|  | 259.41 | 1707.0 | 92.3 |  |
| 300 | 204.8 | 1374.2 | 92.1 | 92.4 |
|  | 218.5 | 1378.1 | 92.6 |  |
| 350 | 214.7 | 1195.5 | 93.5 | 93.3 |
|  | 266.0 | 1542.9 | 93.2 |  |
| 450 | 186.3 | 568.7 | 96.4 | 96.3 |
|  | 275.5 | 878.3 | 96.3 |  |

Example 3

The experiment was performed under the same condition as Example 1 and the solid sample polymerization structure of ODPA-ODA PI film 3 of Example 3 and the moisture content and the imidization rate generated for each temperature when ODPA-ODA PI film 3 are polymerized are described below. It is noted that MWpaa of PI film 3 is 510.46 and MWPI of PI film 3 is 474.43.

TABLE 5

| Curing temperature (° C.) | Sample amount (mg) | Moisture content (μg) | DI (%) | DI (%) average value |
|---|---|---|---|---|
| 200 | 230.3 | 1665.5 | 90.4 | 90.2 |
|  | 249.9 | 1868.0 | 90.1 |  |
| 250 | 146.9 | 1055.3 | 90.7 | 92.7 |
|  | 212.7 | 1498.4 | 94.7 |  |
| 300 | 254.2 | 1389.4 | 92.8 | 93.1 |
|  | 250.8 | 1260.6 | 93.3 |  |
| 350 | 240.0 | 1237.8 | 93.2 | 93.3 |
|  | 237.0 | 1195.4 | 93.3 |  |
| 450 | 257.0 | 505.0 | 97.4 | 97.4 |

<Detailed Examination>

Figure 5:
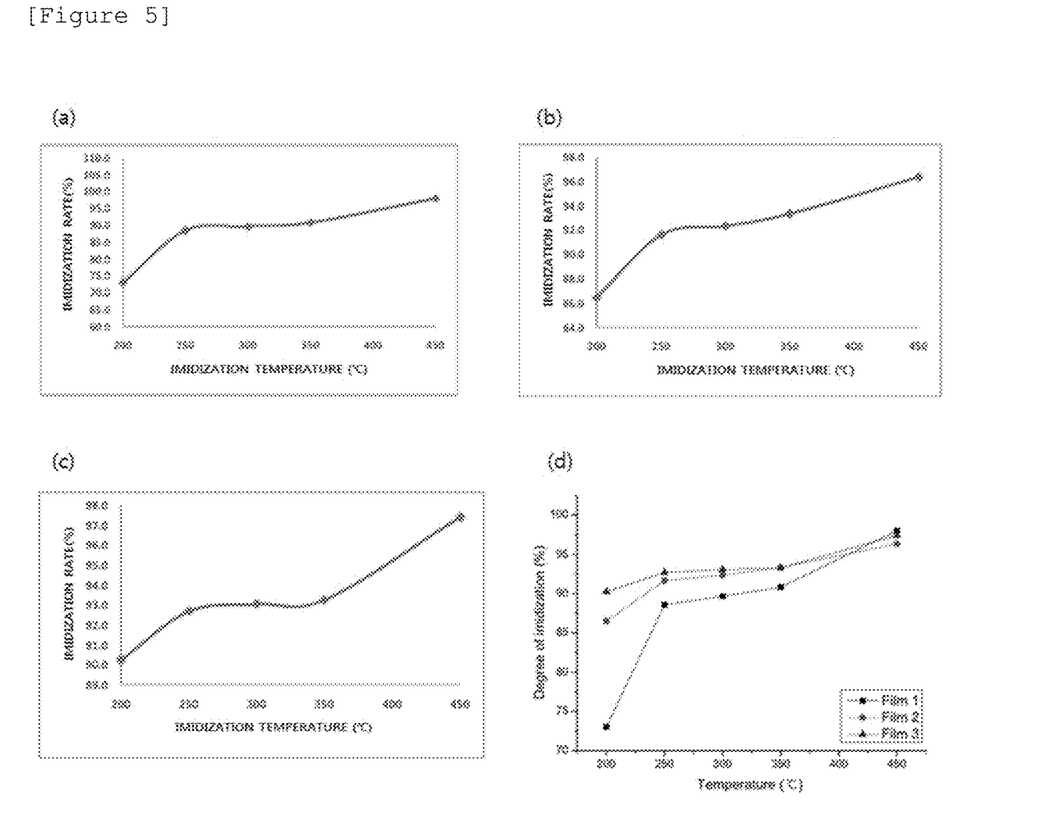
FIG. 5 is a graph illustrating an experimental result of an imidization rate for each temperature according to an example.

Referring to FIG. 5, FIG. 5(a) illustrates the experimental result of PI film 1, FIG. 5(b) illustrates a result of PI film 2, and FIG. 5(c) illustrates the result of PI film 3. As described in Experimental Example 2, it may be verified that as the moisture content is low and the molecular weights of polyacrylamide (PAA) and polyimide (PI) are low, the imidization rate is increased.

Further, FIG. 5(d) is a graph of comparing imidization rate graphs for each of temperatures of PI films 1 to 3 and it may be verified that the most moisture is generated at 200° C. and as the temperature increases, the moisture content decreases, and as a result, the imidization rate increases.

Moreover, it may be verified that as the temperatures of PI films 1 to 3 increase, a difference in imidization rate value is reduced and the difference in imidization rate value is smallest at the temperature of 450° C.

The present invention has been described with reference to the preferred embodiments. However, it will be appreciated by those skilled in the art that various modifications and changes of the present invention can be made without departing from the spirit and the scope of the present invention which are defined in the appended claims.

The invention claimed is:

1. An apparatus for measuring moisture of a solid sample, the apparatus comprising:
an introduction unit into which the solid sample is capable of being introduced;
a furnace unit to which the solid sample is capable of being fixed, the furnace unit comprising a moisture transport pipe for supplying a moisture transport gas into the furnace unit, the furnace unit for heating and cooling the solid sample;
a control unit for controlling a threshold temperature of the furnace unit; an O-ring unit sealed between the introduction unit and the furnace unit;
a three-way valve connected to the furnace unit via the moisture transport pipe, the three-way valve for receiving and controlling moisture evaporated from the solid sample, the moisture transport gas for transporting the moisture evaporated from the solid sample to the three-way valve; and
a Karl-Fischer unit connected to the three-way valve via a metering transport pipe, the Karl-Fischer unit for measuring a detected moisture content of the solid sample from the moisture evaporated form the solid sample,
wherein the O-ring unit includes an O-ring cooling unit positioned adjacent to the O-ring unit, the O-ring cooling unit for cooling the O-ring unit,
wherein the threshold temperature of the furnace unit can be set to at least one temperature selected from the group consisting of a first threshold temperature, a second threshold temperature, and a third threshold temperature,
wherein the control unit controls the three-way valve to allow a purge of moisture from the furnace unit to outside the apparatus and to prevent transport of moisture from the furnace unit to the Karl-Fischer unit when the furnace unit is heated up to the first threshold temperature or heated up to the third threshold temperature or higher, and
wherein the control unit controls the three-way valve to prevent a purge moisture from the furnace unit to outside the apparatus and to permit transport of moisture from the furnace unit to the Karl-Fischer unit when the furnace unit is heated up to the second threshold temperature and the third threshold temperature.

2. The apparatus of claim 1, wherein the furnace unit comprises:
a body for fixing the solid sample,
a heating unit positioned outside the body, the heating unit for heating the body, and a cooling unit positioned outside the body, the cooling unit for cooling the body.

3. The apparatus of claim 2, wherein the cooling unit and the O-ring cooling unit use at least one of a water cooling type and an air cooling type for cooling the body and the O-ring, respectively.

4. The apparatus of claim 1, wherein the moisture transportation gas pipe includes a moisture trap unit to remove moisture in the moisture transport gas.

5. The apparatus of claim 1, wherein the three-way valve comprises:
a moisture transport port for receiving the moisture from the furnace unit,
a purge port for purging the moisture from the furnace unit outside of the apparatus, and
a metering port for transporting the moisture from the furnace unit to the Karl-Fischer unit.

6. The apparatus of claim 5, wherein the control unit controls the threshold temperature of the furnace unit by controlling the heating unit and the cooling unit and by controlling the three-way valve.

7. The apparatus of claim 6, wherein the control unit heats or cools the furnace unit by setting a temperature of the heating unit to the first threshold temperature, then heating to the second threshold temperature, then heating to the third threshold temperature, and then cools the furnace unit back to the first threshold temperature.

8. The apparatus of claim 7, wherein the control unit controls the purge port to be on and the metering port to be off when the furnace unit is heated up to the first threshold temperature or heated up to the third threshold temperature or higher, and
controls the purge port to be off and the metering port to be on when the furnace unit is heated up to the second threshold temperature and the third threshold temperature.

9. A method for analyzing a solid sample,
comprising: fixing the solid sample to a body of a furnace unit of an apparatus;
heating the body to heat the solid sample;
transporting moisture evaporated from the solid sample through a three-way valve of the apparatus, wherein the three-way valve includes a purge port for purging the moisture to outside of the apparatus, and a metering port for transporting the moisture to a Karl-Fischer unit of the apparatus;

measuring a detected moisture content of the solid sample through the moisture transported to the Karl-Fischer unit; and cooling the body, wherein during cooling of the body, an O-ring unit positioned between an introduction unit and the body is cooled, wherein the introduction unit is a unit of the apparatus for introducing the solid sample into the body, wherein transporting moisture evaporated from the solid sample further comprises:

transporting the evaporated moisture to outside of the apparatus by controlling, by a control unit, the purge port to be on and the metering port to be off in the three-way valve when the body is at a first threshold temperature, transporting the evaporated moisture to the Karl-Fischer unit by controlling, by the control unit, the purge port to be off and the metering port to be on when the body is at a second threshold temperature that is higher than the first threshold temperature, transporting the evaporated moisture to the Karl-Fischer unit by controlling, by the control unit, the purge port to be off and the metering port to be on when the body is at a third threshold temperature higher than the second threshold temperature, and transporting the evaporated moisture to outside of the apparatus by controlling, by the control unit, the purge port to be on and the metering port to be off when the body is at the third threshold temperature or higher.

10. The method of claim 9, wherein the heating of the body comprises:

heating the body from a reference temperature up to a first threshold temperature, heating the body from the first threshold temperature up to a second threshold temperature, and heating the body from the second threshold temperature up to a third threshold temperature.

11. The method of claim 10, wherein the cooling of the body comprises:

introducing at least one of gas and liquid into a cooling unit positioned outside the body to cool the body to at least one temperature selected from the group consisting of the reference temperature and the first threshold temperature.

12. The method of claim 10, further comprising:

analyzing the imidization rate of the solid sample from the detected moisture content.

13. The method of claim 12, wherein in the analyzing of the imidization rate, the imidization rate is analyzed by using the detected moisture content evaporated from the solid sample when the body is at at-least one temperature selected from the group consisting of a second threshold temperature and a third threshold temperature.

14. The method of claim 12, wherein in the analyzing of the imidization rate, the imidization rate is calculated to correspond to a variable determined based on an equation given below, $$DI\ (\%) = \frac{W_{PI}/MW_{PI}}{W_{H2O}(M_{H2O} \times 18) + W_{PI}/MW_{PI}} \quad \text{[Equation 1]}$$

Herein, DI represents the imidization rate, $W_{H2O}$ represents the detected moisture content (g), $M_{H2O}$ represents mol of $H_2O$ evaporated per unit, $W_{PI}$ represents polyimide mass (g) in the solid sample, $MW_{PI}$ represents a molecular weight of the polyimide unit, and $W_{sample}$ represents measured solid sample mass (g).

* * * * *